(12) United States Patent
Kleinmann et al.

(10) Patent No.: US 11,607,468 B2
(45) Date of Patent: Mar. 21, 2023

(54) DECONTAMINATION DEVICE, ISOLATOR SYSTEM, AND OPERATING METHOD

(71) Applicant: Metall + Plastic GmbH, Radolfzell (DE)

(72) Inventors: Stefan Kleinmann, Radolfzell (DE); Thomas Kassner, Radolfzell (DE)

(73) Assignee: Metall + Plastic GmbH, Radolfzell (DE)

( * ) Notice: Subject to any disclaimer, the term of this patent is extended or adjusted under 35 U.S.C. 154(b) by 355 days.

(21) Appl. No.: 16/638,895

(22) PCT Filed: Aug. 1, 2018

(86) PCT No.: PCT/EP2018/070831
§ 371 (c)(1),
(2) Date: Feb. 13, 2020

(87) PCT Pub. No.: WO2019/034424
PCT Pub. Date: Feb. 21, 2019

(65) Prior Publication Data
US 2021/0128759 A1 May 6, 2021

(30) Foreign Application Priority Data

Aug. 14, 2017 (DE) ............... 10 2017 118 481.3

(51) Int. Cl.
*A61L 2/00* (2006.01)
*A61L 2/07* (2006.01)
(Continued)

(52) U.S. Cl.
CPC .......... *A61L 2/0023* (2013.01); *A61L 2/0094* (2013.01); *A61L 2/07* (2013.01); *A61L 2/22* (2013.01);
(Continued)

(58) Field of Classification Search
CPC ................................ A61L 2202/122
See application file for complete search history.

(56) References Cited

U.S. PATENT DOCUMENTS

2005/0084431 A1* 4/2005 Hill .................. A61L 2/24
422/305
2005/0133729 A1* 6/2005 Woodworth .......... A61M 5/008
250/455.11
(Continued)

FOREIGN PATENT DOCUMENTS

EP 1787731 A2 5/2007
WO 03030184 A1 4/2003
(Continued)

OTHER PUBLICATIONS

WhiteTmixTPT, Batman—The Cobblepot Caper [Game], Dec. 29, 2016, Youtube, https://www.youtube.com/watch?v=86kkJXvqmyU (Year: 2016).*

(Continued)

*Primary Examiner* — Kevin Joyner
*Assistant Examiner* — Changru Chen
(74) *Attorney, Agent, or Firm* — Bachman & LaPointe, P.C.

(57) ABSTRACT

A decontamination device (1) for decontaminating products in the form of consumer goods and/or consumer good packaging having consumer goods located therein prior to supplying the consumer goods into an isolator, the decontamination device comprising several decontamination chambers (3, 4, 5, 6) each having a closable inlet opening (9) and a closable outlet opening (10), and each comprising application means (7) for applying a decontamination agent, to the decontamination chambers (3, 4, 5, 6), and the decontamination device (1) comprising a distributor chamber (11) disposed upstream of the decontamination chambers (3, 4, 5, 6) and having a supply opening (24) for products to (Continued)

be decontaminated, the distributor chamber (11) comprising distributor means (15) for distributing the products to the different decontamination chambers (3, 4, 5, 6), and the decontamination device (1) comprising a discharge chamber (12) disposed downstream of the decontamination chambers (3, 4, 5, 6) and having a discharge opening (2) and comprising transport means (16) for transporting the decontaminated products out of the decontamination chambers (3, 4, 5, 6), the distributor chamber (11) and/or the discharge chamber (12) being assigned means (17) for reducing a decontamination agent concentration by means of which the decontamination agent is conveyed through a catalytic converter in air circulation mode and/or decontamination agent is displaced by supplying fresh air.

17 Claims, 1 Drawing Sheet

(51) Int. Cl.
*A61L 2/22* (2006.01)
*A61L 2/26* (2006.01)

(52) U.S. Cl.
CPC ........... *A61L 2/26* (2013.01); *A61L 2202/121* (2013.01); *A61L 2202/122* (2013.01); *A61L 2202/15* (2013.01); *A61L 2202/21* (2013.01); *A61L 2202/23* (2013.01)

(56) References Cited

U.S. PATENT DOCUMENTS

| | | |
|---|---|---|
| 2008/0003135 A1 | 1/2008 | Patrice |
| 2011/0058986 A1* | 3/2011 | Yokoi .................... C12M 37/00 422/111 |
| 2016/0101202 A1* | 4/2016 | Gil ........................... A61L 2/10 250/455.11 |

FOREIGN PATENT DOCUMENTS

| | | |
|---|---|---|
| WO | 2009030599 A1 | 3/2009 |
| WO | 2011085735 A1 | 7/2011 |

OTHER PUBLICATIONS

International search report for patent application No. PCT/EP2018/070831 dated Nov. 13, 2018.

\* cited by examiner

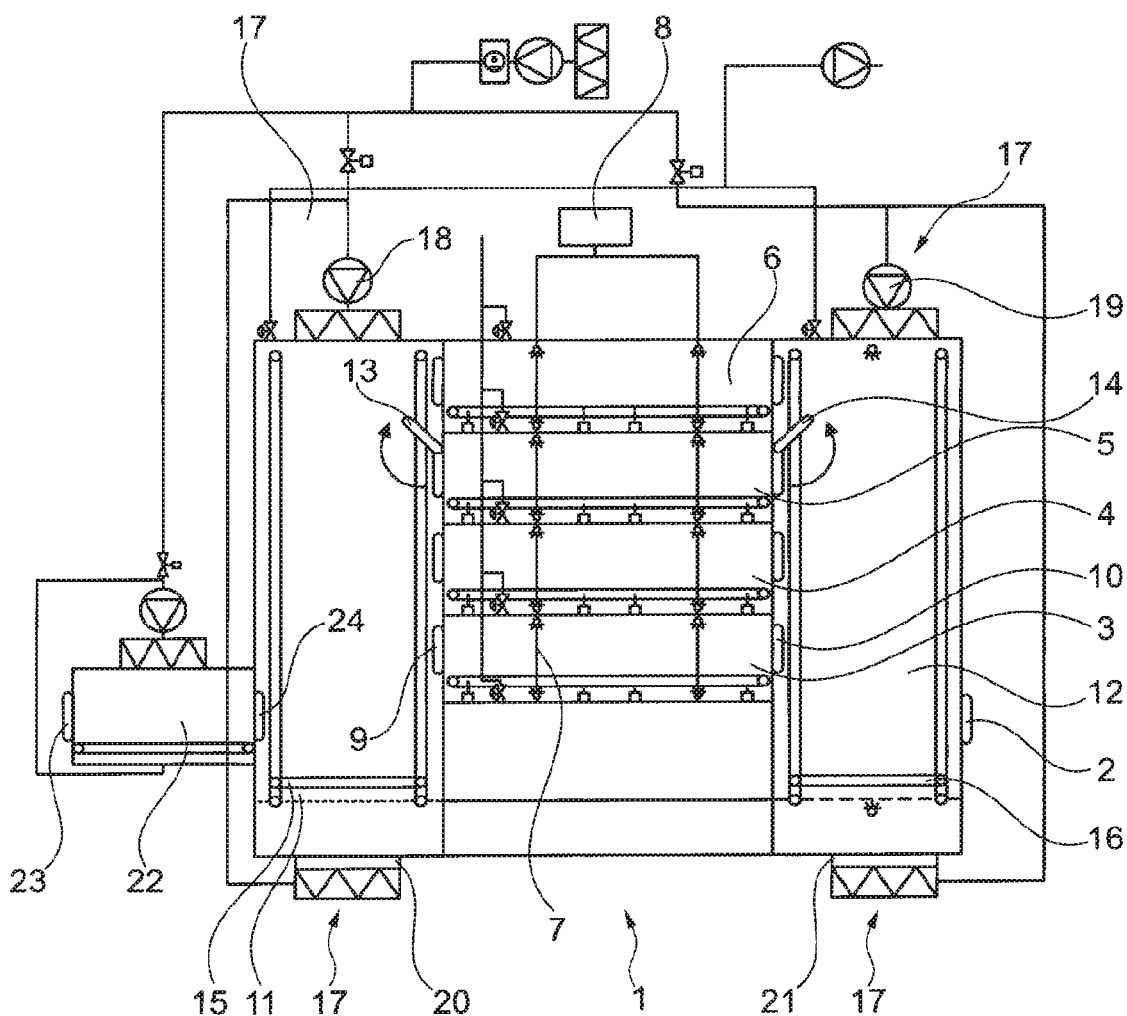

DECONTAMINATION DEVICE, ISOLATOR SYSTEM, AND OPERATING METHOD

BACKGROUND OF THE INVENTION

The invention relates to a decontamination device for decontaminating products in the form of consumer goods and/or secondary consumer good packaging having consumer goods located therein, said consumer goods being pre-sterilized, i.e. packaged in a sterile manner, and being particularly preferably realized as immediate packaging, prior to supplying the consumer goods into an isolator, in particular for pharmaceutical applications.

Furthermore, the invention relates to an isolator system, in particular for pharmaceutical applications, comprising an isolator and a decontamination device according to the invention which is disposed upstream of the isolator.

The invention also relates to a method for operating a decontamination device according to the invention and/or an isolator system according to the invention.

It is known for consumer goods such as packaging or containers of medicinal products and/or their secondary packaging to be decontaminated before the consumer goods are supplied to an isolator, for which purpose a decontamination agent, usually in the form of hydrogen peroxide steam, is applied to the consumer goods or the secondary consumer good packaging in a decontamination chamber and the consumer goods or the secondary consumer good packaging are then supplied to the isolator in a sterile manner. If secondary packing is decontaminated, the consumer goods are unpacked from the secondary packaging to the isolator, said secondary packaging being sterile on the inside and having been decontaminated in the aforementioned manner. Concerning known decontamination devices, the long period of time between the loading of the decontamination chamber and the transfer into the isolator is considered disadvantageous. This is particularly due to the fact that the decontamination chamber is free from decontamination agent when it is loaded in order to avoid an exposure of an operator and, after closing the decontamination chamber, the decontamination agent concentration in the decontamination chamber has to be increased (again), has to be maintained during the decontamination time and then has to be reduced again before a connection to the isolator is opened in order to avoid a leakage of decontamination agent into the isolator because the decontamination agent, usually hydrogen peroxide, can have a negative impact on the medical agents located in the isolator.

From EP 1 787 731 A2, a washing apparatus, in particular for heat disinfection, is known, which comprises a plurality of washing machines which are disposed aligned along an axis of alignment, and which comprises a movement device for moving an object-bearing container parallel to the axis of alignment. The movement device is provided with a trolley for transporting the container and with sliding means guided by a guide element which extends parallel to the axis of alignment.

US 2008/003135 A1 discloses a product sterilization or pasteurization method. The described method includes the following method steps: transferring a product from outside to inside into a pressurized inlet compartment of a chamber through at least one pressurized air lock; loading the product onto a conveyor in order to transfer the product through the chamber from the inlet compartment into an outlet compartment; heating the product by dipping the product in hydrostatic columns while applying variable pressure and temperature; passing the product through an intermediate pressurized compartment; cooling the product by dipping the product in hydrostatic columns while applying variable pressure and temperature; unloading the product from the conveyor in a pressurized outlet compartment; and transferring the product from the outlet compartment to the outside through at least one atmospheric pressurized air lock.

SUMMARY OF THE INVENTION

Starting from the aforementioned state of the art, the object of the invention is to indicate an improved decontamination device, an improved isolator system and an improved operating method which allow for a faster, preferably quasi-continuous loading of the isolator with consumer goods. In particular, the retention time of the products (in particular of the secondary consumer good packaging) in a decontamination chamber of the decontamination device is to be reduced compared to the state of the art.

Concerning the decontamination device, said object is attained by the features disclosed herein, i.e. by means of a decontamination device for decontaminating products, in particular consumer goods and/or secondary consumer good packaging (which are closed and which preferably contain consumer goods such as sterile immediate packaging or containers of pharmaceuticals) prior to supplying the consumer goods into an isolator, in particular one configured for pharmaceutical applications, said decontamination device comprising several decontamination chambers each having a closable inlet opening and a closable outlet opening, and each decontamination chamber comprising application means for applying decontamination agent, in particular decontamination agent steam or aerosol, particularly preferably hydrogen peroxide steam or aerosol, to the decontamination chambers, and the decontamination device having a distributor chamber assigned to the decontamination chambers and having a supply opening for the products to be decontaminated, the distributor chamber comprising distributor means for distributing the products to the different, in particular free, decontamination chambers (in an automated manner) and having a discharge chamber disposed downstream of the decontamination chambers and having a discharge opening, in particular for decontaminated products or consumer goods unpacked from said decontaminated products, comprising transport means for transporting the decontaminated products out of the decontamination chambers, preferably towards the discharge opening and/or towards unpacking means, the distributor chamber and/or the discharge chamber being assigned means for reducing a decontamination agent concentration in the distributor chamber and/or the discharge chamber by means of which the decontamination agent is conveyed through a catalytic converter in air circulation mode and/or decontamination agent is displaced by supplying fresh air.

Concerning the isolator system, said object is also attained by the features disclosed herein.

Concerning the method, said object is attained by the features disclosed herein, i.e. concerning a generic method, by the fact that products to be decontaminated, in the form of consumer goods or secondary consumer good packaging having sterile consumer goods, in particular immediate packaging, located therein, are introduced into the distributor chamber through the supply opening, in particular one after the other, and that said products are distributed to the different decontamination chambers in said distributor chamber by means of the distributor means and are transported inside the discharge chamber towards the discharge opening after a predefined decontamination period by means of the transport means, the decontamination chambers being closed during said period, and that the decontamination agent concentration in the distributor chamber and/or in the in the discharge chamber is, preferably continuously, lowered or reduced.

Advantageous embodiments of the invention are disclosed herein and in the dependent claims.

All combinations of at least two features disclosed in the description, the claims and/or the figures constitute part of the scope of the invention.

In order to avoid repetitions, disclosed features relating to the device are also seen as relating to the method and are thus also claimable therefor. In the same manner, disclosed features relating to the method are also seen as relating to the device and are thus also claimable therefor.

The idea of the invention is to provide several, preferably more than two, decontamination chambers which can be loaded, in particular one after the other, with products to be decontaminated in the form of consumer goods and/or consumer good packaging having sterile consumer goods disposed therein, namely via distributor means disposed in a distributor chamber by means of which the products can be distributed to the different decontamination chambers in an automated manner. The decontamination chambers each have an inlet opening and an outlet opening, both the inlet opening and the outlet opening being closable, the respective inlet opening being opened for loading and closed afterwards and the outlet opening being opened for unloading and closed afterwards. The outlet openings lead to a discharge chamber which is disposed downstream of the decontamination chambers and in which the decontaminated products are collected from the individual decontamination chambers and are or can be transported by means of transport means, preferably towards the discharge opening by means of which the products can be supplied to the isolator (directly or indirectly via a facultative product gate). The products to be decontaminated are particularly preferably consumer good packaging which are supplied to a product gate, which is realized as a unpacking gate, via the discharge opening, pre-sterilized, i.e. sterilized consumer goods, in particular immediate packaging for pharmaceuticals, being either manually or automatically unpacked from the decontaminated products, i.e. the consumer good packaging, inside the product gate, and the sterile, unpacked consumer goods then being transferred from the product gate into the isolator in a sterile manner. An alternative use of the decontamination device according to the invention is also conceivable, said alternative use being characterized in that, instead of the consumer good packaging, the consumer goods being the products are directly decontaminated and are supplied to the isolator via the discharge chamber through an intermediary product gate, if required.

According to the invention, the distributor chamber and the discharge chamber not only have a distribution or collection function with respect to the products, but at least one of these two chambers, in particular both chambers, are assigned means for reducing the decontamination agent concentration in the (respective) chamber air in order to reduce the concentration of decontamination agent in the distributor chamber and/or in the discharge chamber. Said embodiment allows the decontamination device to be realized and operated in such a manner that the decontamination agent concentration in the decontamination chambers can be kept at a permanently high level during operation of the decontamination device; i.e. the decontamination agent concentration in the decontamination chambers does not have to be reduced to almost zero for loading the decontamination chambers and for unloading the decontamination chambers, as was previously the case in the state of the art. Instead, the decontamination chambers can be loaded and unloaded at a high decontamination agent concentration, the ramps which are necessary in the state of the art for increasing and reducing the decontamination agent concentration thus being avoidable and the retention time of the products in the respective decontamination chambers thus being reducible. The decontamination agent flowing into the distributor chamber via the inlet openings of the decontamination chambers during loading and/or the decontamination agent flowing into the discharge chamber via the outlet openings during unloading and the resulting decontamination agent concentration in the distributor chamber and/or in the discharge chamber are reducible by means of the reduction means, according to the invention by conveying the decontamination agent through a catalytic converter in air circulation mode and/or by displacing decontamination agent by supplying fresh air.

Overall, the decontamination device according to the invention and an isolator system having said decontamination device and the operating method according to the invention allow for a faster loading of an isolator and, at the same time, for a reduced retention time of the products to be decontaminated in the decontamination chambers. Furthermore, a quasi-continuous operation or a quasi-continuous supply of consumer goods to the isolator can be ensured by the consecutive loading of a plurality of decontamination chambers which decontaminate the products in a delayed and overlapping manner. As explained above, it is generally possible to decontaminate the consumer goods in a direct manner and then to supply said consumer goods to the isolator; in a preferred embodiment, the consumer goods to be supplied to the isolator are disposed in a (pre-sterilized) secondary consumer good packaging and the secondary packaging is decontaminated inside the decontamination chamber, after which the consumer goods are unpacked, either in the isolator or preferably before said consumer goods are supplied to the isolator, for example in the discharge chamber or in a facultative product lock which is realized as an unpacking lock and which is disposed downstream of the discharge chamber.

In an advantageous embodiment of the invention for realizing the decontamination device in a space-saving manner, the decontamination chambers are disposed above one another along a vertical and the distributor means and the transport means each comprise a product lift by means of which the products (concerning the distributor means) can be supplied to the individual decontamination chambers disposed above one another and (concerning the transport means) can be transported from said individual decontamination chambers disposed above one another towards the discharge opening of the discharge chamber. The product lift can also be realized as a paternoster system; however, a conventional lift system is preferred, which comprises a product receptacle or platform and in which the production receptacle is displaced back and forth on the same displacement line along the vertical without being diverted as in a paternoster.

With respect to the specific embodiment of the means for reducing the decontamination agent concentration in the distributor chamber and/or in the discharge chamber, different possibilities are available. In a particularly preferred embodiment of said reduction means, the reduction means comprise air circulation generator means, in particular in the form of a fan, by means of which an air circulation volume flow of the respective chamber air through catalyst means for degrading the decontamination agent can be generated. In said embodiment, the reduction means comprise such catalyst means. The catalyst means, which contain palladium, for example, are preferably realized in such a manner that the decontamination agent, in particular hydrogen peroxide, is broken down into its individual components, preferably into water and oxygen in the case of hydrogen peroxide. Additionally or alternatively, the reduction means can comprise fresh air supply means for displacing chamber air containing decontamination agent from the respective chamber, in particular into the atmosphere, particularly preferably via a catalytic converter for degrading the decontamination agent.

As explained above, the distributor chamber preferably comprises means for reducing the decontamination agent concentration. Since a certain decontamination agent concentration in the distributor chamber cannot be avoided in practice, however, a product lock is provided or disposed upstream of the distributor chamber in an embodiment of the invention for reducing a risk, in particular a risk of chemical burns, for an operator or a loading person, said product lock having a closable entrance door, and a product located in the product lock being suppliable to the distributor chamber via the supply opening of the distributor chamber by way of the product lock when the entrance door is closed. The product lock comprises means for reducing the decontamination agent concentration, for example in the form of air circulation generator means and catalyst means for degrading or for breaking down the decontamination agent and/or fresh air supply means for reducing the decontamination agent concentration in the lock before the entrance door is opened. Due to the smaller internal volume of the product lock compared to the distributor chamber, the decontamination agent concentration can be reduced to safe levels, in particular to almost zero, before the entrance door is opened and/or can be opened for the supply of new products or products to be decontaminated.

In a particularly preferred embodiment, a product lock is disposed downstream of the discharge chamber, said product lock being preferably separable from an isolator via at least one (additional) product lock door and being preferably accessible via the discharge opening of the discharge chamber. Unpacking means for an automated unpacking of consumer goods from a secondary packaging, which has been decontaminated within the scope of the decontamination process, are preferably disposed in the product lock. Additionally or alternatively, a manual unpacking from the outside, in particular by means of gloves being disposed in a lateral wall, is possible or can be realized. A decontamination agent concentration in the product lock can preferably be reduced by corresponding means before opening a gate door towards the isolator and preferably after closing the connection to the discharge chamber. In other words, the product lock comprises means for reducing the decontamination agent concentration, according to the invention in the form of air circulation generator means and catalyst means for degrading or for breaking down the decontamination agent and/or fresh air supply means for reducing the decontamination agent concentration in the lock.

The decontamination device preferably comprises means for transferring products from the distributor means into a respective decontamination chamber. Said transfer means can be part of the distributor means, for example if a product receptacle of the distributor means comprises transport rollers which are driven in a corresponding manner and/or a driven transport belt and/or a product slider. It is also conceivable to dispose said transfer means outside the distributor means, in particular in an area upstream of a respective decontamination chamber in the distributor chamber. Additionally or alternatively, the decontamination device comprises means for removing the decontaminated products from the decontamination chambers or for transferring the products onto the transport means, said means being realizable in the decontamination chambers and/or at the transport means, for example in the form of transport rollers and/or a conveyor belt and/or a slider or a traction device. Additionally or alternatively, the decontamination device preferably comprises means for conveying the products from the respective inlet opening of the decontamination chamber to the respective outlet opening. Here, too, sliders and/or traction means and/or driven rollers and/or driven belts etc. can be used.

As already mentioned, the decontamination device can preferably be operated in such a manner that the decontamination agent concentration in the decontamination chambers remains at a high level during operation of the device, i.e. also during loading and unloading of the decontamination chambers. To this end, application means for applying decontamination agent to the decontamination chambers are particularly preferably controlled in such a manner that an, in particular monitored or measured, decontamination agent concentration in the decontamination chambers is or can be kept above a limit value, in particular from a range between 300 ppm and 1200 ppm, particularly preferably between 500 ppm and 1000 ppm, during loading and/or unloading of the decontamination chambers.

In a particularly preferred embodiment of the decontamination device, the decontamination chambers of said decontamination device each comprise lifting means for lifting the products to be decontaminated, the lifting means being preferably realized in such a manner that, at least during a period of time of the decontamination phase, a lower bottom side along the vertical levitates or is not covered in order to ensure a contact with decontamination agents.

Furthermore, the invention relates to an isolator system, in particular for pharmaceutical applications, comprising an isolator and a decontamination device which is realized according to the idea of the invention and which is connected to said isolator in such a manner that decontaminated products in the form of consumer goods or, if the products are realized as secondary consumer good packaging, sterile or pre-sterilized packaging goods, in particular immediate packaging, which are preferably previously unpacked, can be supplied to the discharge chamber either directly or via an additional (facultative) product lock in the isolator, in particular into a manipulator chamber of the isolator, in a sterile manner. The consumer goods are particularly preferably unpacked from the respective, decontaminated secondary packaging (in a manual or automated manner) in the product lock before said products are supplied to the isolator. The isolator, preferably a manipulator chamber of the isolator, preferably comprises devices for producing and/or filling and/or processing pharmaceutical agents. In any event, the products which are transported from the decontamination device according to the invention into the isolator are preferably used for pharmaceutical applications, in particular for being filled with a pharmaceutical ingredient inside the isolator. Particularly preferably, consumer goods, in particular packaging, are unpacked from a consumer good packaging, which has been decontaminated in a decontamination chamber of the decontamination device and which contains the already sterile consumer goods, and are used as intended as early as inside the isolator or alternatively before they are supplied, either in the discharge chamber or in a facultative product lock which is disposed downstream of said discharge chamber. The isolator, which is configured in particular for pharmaceutical applications, comprises a chamber which can be decontaminated, in particular the aforementioned manipulator chamber, and/or a plenum chamber which is separated from the manipulator chamber by a membrane for laminarizing an air flow. An air circulation fan for complementing the air flow is preferably disposed in an air circulation generating chamber above the aforementioned plenum chamber. The manipulator chamber is particularly preferably connected in an air-conducting manner to the aforementioned air circulation generating chamber, which is preferably provided, via a backflow channel which is realized, further preferably, between two transparent panes or alternatively formed by a pipeline. For realizing the feature of the configuration of the isolator for pharmaceutical applications, a dosing and/or a filling device for a pharmaceutical agent and/or a production device for such an agent is preferably disposed in the manipulator chamber. In a particularly preferred embodiment, the manipulator chamber is accessible to an operator by means of gloves for manual intervention from the outside, the gloves or so-called glove ports being disposed or fixed in a lateral wall of the manipulator. A product lock, which is preferably realized as an unpacking lock, is preferably disposed between the discharge chamber and the isolator, consumer goods, in particular immediate packaging, being unpacked in said product lock, preferably in an automated or, alternatively, in a manual manner, from a secondary packaging, which has previously been decontaminated in one of the decontamination chambers. The product lock is assigned means for reducing the decontamination agent concentration, in particular after a separation from the discharge chamber and before the opening of a connection to the isolator.

The invention also relates to a method for operating a decontamination device according to the invention and/or an isolator system according to the invention. Within the scope of the method, products to be decontaminated in the form of consumer goods, such as product packaging and/or secondary consumer good packaging containing the consumer goods in a sterile manner, are introduced into the distributor chamber through the supply opening, in particular one after the other, where they are distributed, in particular along a vertical, to the decontamination chambers, which are preferably disposed above one another along the vertical, by means of the distributor means and are transported inside the discharge chamber towards the discharge opening, in particular along a vertical, by means of the transport means after a predefined decontamination period, during which the decontamination chambers, i.e. their respective inlet openings and/or outlet openings, are closed, and are supplied to the isolator via the discharge opening, the decontamination agent concentration being conveyed into the distributor chamber and/or in the discharge chamber, in particular in a continuous manner and/or during a loading and/or unloading process of the decontamination chambers and/or during a decontamination phase in which at least one of the decontamination chambers is closed, particularly preferably by conveying the respective chamber air in air circulation mode through a catalytic converter or catalyst means which are configured for degrading decontamination agent.

During the normal operation of the decontamination device, i.e. in particular during the loading and unloading of the decontamination chambers from the distributor chamber or into the discharge chamber, the decontamination agent concentration is particularly preferably kept above a limit value, in particular between 300 ppm and 1200 ppm, in order to avoid ramps for increasing the concentration and/or for reducing the concentration which are necessary in the state of the art. Additionally or alternatively, an active reduction of the decontamination agent concentration before the loading and/or unloading of the decontamination chambers by using corresponding reduction means, such as fresh air supply means and/or air circulation generating means, by means of which the decontamination agent or the chamber air of the decontamination chambers is conveyed through a catalytic converter for degrading the decontamination agent in air circulation mode, is omitted. The only (rather minor) reduction of the decontamination agent concentration is caused by the brief opening of the connection of the respective decontamination chamber to the distributor chamber and/or to the discharge chamber.

BRIEF DESCRIPTION OF THE DRAWINGS

Further advantages, features and details of the invention can be derived from the following description of a preferred exemplary embodiment and from the drawings.

FIG. 1 shows a schematic configuration of a preferred embodiment of a decontamination device according to the idea of the invention.

DETAILED DESCRIPTION

In FIG. 1, a decontamination device 1 according to the idea of the invention is shown. Said decontamination device 1 is disposed upstream of a pharmaceutic isolator (not shown) which can be supplied with decontaminated products via a discharge opening 2.

Decontamination device 1 comprises several decontamination chambers 3, 4, 5, 6 which are disposed above one another along a vertical, application means 7 for applying decontamination agent to each of the decontamination chambers 3, 4, 5, 6 being assigned to said decontamination chambers 3, 4, 5, 6. In the present case, application means 7 comprise a flash evaporator 8 for generating decontamination agent steam—hydrogen peroxide steam in the present case—and distributor lines which lead to decontamination chambers 3, 4, 5, 6. Additionally or alternatively, application means 7 can comprise fogging nozzles for generating a decontamination agent aerosol, in particular a hydrogen peroxide aerosol.

Each decontamination chamber 3, 4, 5, 6 has an openable and closable inlet opening 9 and an openable and closable outlet opening 10. Products to be decontaminated can be supplied from a distributor chamber 11 to decontamination chambers 3, 4, 5, 6 via opened inlet openings 9, whereas decontaminated products can be transferred into a discharge chamber 12 having discharge opening 2 via opened outlet openings 10. During a decontamination phase, in which at least one product to be decontaminated is located inside a respective decontamination chamber 3, 4, 5, 6, inlet opening 9 and outlet opening 10 of respective decontamination chamber 3, 4, 5, 6 are closed. In the present case, inlet openings 9 and outlet openings 10 comprise corresponding doors 13, 14, in an exemplary manner in the form of flaps, for being opened and closed. Alternative closing elements (doors) can be realized.

Distributor means 15 in the form of a product lift which can be displaced along a vertical are located in distributor chamber 11, said product lift being stoppable at individual inlet openings 9 and decontamination chambers 3, 4, 5, 6 for distributing the products to be decontaminated. Transport means 16, also in the form of a product lift, are provided in discharge chamber 12 in order to be able to convey or transport the decontaminated products from decontamination chambers 3, 4, 5, 6 towards discharge opening 2.

Means 17 for reducing the decontamination agent concentration are assigned both to distributor chamber 11 and to discharge chamber 12, said means 17 each comprising an air circulation fan 18, 19 for generating an air circulation volume flow through catalyst means 20, 21 for degrading decontamination agents, in the present case for breaking down hydrogen peroxide into the components water and oxygen. Without means 17, the decontamination agent concentration in distributor chamber 11 and in discharge chamber 12 would approximate the decontamination agent concentration in decontamination chambers 3, 4, 5, 6 due to the temporary opening of inlet openings 9 and outlet openings 10—said approximation is to be avoided. During operation, the decontamination agent concentration in decontamination chambers 3, 4, 5, 6 is largely maintained and does preferably not drop below a predefined limit value. A reduction of the decontamination agent concentration, in particular the hydrogen peroxide concentration, before loading and/or unloading decontamination chambers 3, 4, 5, 6, i.e. before opening (inlet) door 13 and (outlet) door 14, is deliberately omitted. This is supported by the fact that the opening times of inlet openings 9 and outlet openings 10 are limited and that said openings are closed most of the time during operation. The decontamination agent concentration in decontamination chambers 3, 4, 5, 6 is preferably measured and decontamination agent is refilled accordingly. It is also conceivable to refill or resupply decontamination agent at regular intervals, without performing a measurement, based on experience or calculations.

As shown in FIG. 1, both distributor chamber 11 and discharge chamber 12 are assigned air filters, preferably high-efficiency particulate air filters, by means of which the air is additionally conveyed to catalyst means 20, 21 in air circulation mode.

In the present case, products to be decontaminated are supplied to distributor chamber 11 via a facultative product lock 22 which has an entrance door 23 and which is additionally provided or disposed upstream of distributor chamber 11, the decontamination agent concentration in product lock 22 being reduced before the opening of entrance door 23 to such a degree that said concentration is not dangerous for an operator, in the present case by conveying chamber air through a corresponding catalytic converter in air circulation mode. The products to be decontaminated are then transported from product lock 22 into distributor chamber 12 to distributor means 15 via a closable supply opening 24.

As can be seen, conveyor means in the form of rotating continuous belts are provided on distributor means 15 and transport means 16 and in respective decontamination chambers 3, 4, 5, 6. Alternative conveyor or transfer means can be realized. Concerning the distributor means, the conveyor means are used for conveying the products to be decontaminated into respective decontamination chambers 3, 4, 5, 6. In decontamination chambers 3, 4, 5, 6, the conveyor means are used for transporting the products from respective inlet opening 9 to respective outlet opening 10. The conveyor means of transport means 16 are used for transporting the products to or through discharge opening 2. Furthermore, conveyor means are provided in product lock 22 in order to be able to load distributor chamber 11 in an automatic manner with products to be decontaminated, in particular secondary consumer good packaging holding consumer goods which are packaged in such a sterile manner, in particular immediate packaging, when entrance door 23 is closed.

A product lock (not shown) is preferably disposed downstream of discharge chamber 12, in particular of discharge opening 2 of discharge chamber 12, said product lock being used for supplying the consumer goods to the isolator and/or said consumer goods being unpacked from the previously decontaminated secondary consumer good packaging, in particular automatically by means of a corresponding unpacking robotic system or machinery, in said product lock. The product lock is separated from the isolator via at least one lock door, the product lock being preferably assigned means for degrading decontamination agent, in particular similarly to the product lock by conveying the internal volume or gas of the product lock through a catalytic converter in air circulation mode and/or by displacing decontamination agent by means of sterile fresh air. The decontamination agent is preferably degraded in the product lock before the product lock door to the isolator is opened and/or after closing the connection between the discharge chamber and the product lock.

In an alternative embodiment, the consumer goods can be unpacked from the secondary consumer good packaging in the discharge chamber, preferably, but not necessarily, without a product lock which is disposed downstream of the discharge chamber. If the products are realized as secondary consumer good packaging, it is also conceivable to unpack the consumer goods from the products, i.e. the secondary consumer good packaging, in the isolator with or without realizing a product lock which is disposed between the discharge chamber and the isolator.

REFERENCE SIGNS 1 decontamination device
2 discharge opening of the discharge chamber
3 decontamination chamber
4 decontamination chamber
5 decontamination chamber
6 decontamination chamber
7 application means
8 flash evaporator
9 inlet opening
10 outlet opening
11 distributor chamber
12 discharge chamber
13 door
14 door
15 distributor means
16 transport means
17 means for reducing the decontamination agent concentration
18 air circulation fan
19 air circulation fan
20 catalyst means
21 catalyst means
22 product lock
23 entrance door of the product lock
24 supply opening of the distributor chamber

The invention claimed is:
1. A decontamination device (1) for decontaminating products in the form of consumer goods and/or consumer good packaging having consumer goods located therein prior to supplying the consumer goods into an isolator, the decontamination device comprising:

a plurality of decontamination chambers (3, 4, 5, 6) each having a closable inlet opening (9) and a closable outlet opening (10), and each comprising application means (7) for applying a decontamination agent, to the decontamination chambers (3, 4, 5, 6);

a distributor chamber (11) disposed upstream of the decontamination chambers (3, 4, 5, 6) and having a supply opening (24) for products to be decontaminated, the distributor chamber (11) comprising distributor means (15) for distributing the products to the different decontamination chambers (3, 4, 5, 6); and a discharge chamber (12) disposed downstream of the decontamination chambers (3, 4, 5, 6) and having a discharge opening (2) and comprising transport means (16) for transporting the decontaminated products out of the decontamination chambers (3, 4, 5, 6), the distributor chamber (11) and/or the discharge chamber (12) being assigned means (17) for reducing a decontamination agent concentration by means of which the decontamination agent is conveyed through a catalytic converter in air circulation mode and/or decontamination agent is displaced by supplying fresh air, and wherein the distributor chamber (11) is separated from the decontamination chambers (3, 4, 5, 6) by the closable inlet opening (9) of each of the decontamination chambers (3, 4, 5, 6).

2. The decontamination device according to claim 1, wherein the decontamination chambers (3, 4, 5, 6) are disposed above one another along a vertical and wherein the distributor means (15) and the transport means (16) each comprise a product lift by means of which the products can be supplied to the individual decontamination chambers (3, 4, 5, 6) disposed above one another or by means of which the products can be transported from the decontamination chambers (3, 4, 5, 6) to the discharge opening (2).

3. The decontamination device according to claim 1, wherein the means (17) for reducing the decontamination agent concentration comprise air circulation generator means for generating an air circulation volume flow through catalyst means (20, 21) for degrading the decontamination agent and/or fresh air supply means for rinsing a chamber volume by means of fresh air.

4. The decontamination device according to claim 3, wherein the fresh air is sterile.

5. The decontamination device according to claim 1, wherein a product lock (22) having an entrance door (23) is disposed upstream of the distributor chamber (11), said product lock being loadable with products to be decontaminated, and wherein the products from the product lock (22) can be supplied to the distributor chamber (11) via the supply opening (24) when the entrance door (23) is closed and/or wherein a product lock by means of which the consumer goods can be supplied to an isolator and/or in which consumer goods, can be unpacked from the decontaminated products, manually or in an automated manner via unpacking means before said products are supplied to the isolator is disposed downstream of the discharge chamber (12).

6. The decontamination device according to claim 1, wherein means for transferring products into the decontamination chambers (3, 4, 5, 6) are provided, and/or means for removing the decontaminated products from the decontamination chambers (3, 4, 5, 6) are provided, and/or means for conveying the products from the respective inlet opening (9) to the respective outlet opening (10) are provided.

7. The decontamination device according to claim 6, wherein the means for transferring products into the decontaminated chambers (3, 4, 5, 6) are provided on the distributor means (15), and/or wherein means for removing the decontaminated products from the decontaminated chambers (3, 4, 5, 6) are provided on the transport means (16), and/or means for conveying the products from the respective inlet opening (9) to the respective outlet opening (10) are provided in the decontamination chambers (3, 4, 5, 6).

8. The decontamination device according to claim 1, wherein lifting means for lifting the products are disposed in the decontamination chambers.

9. The decontamination device according to claim 1, wherein the consumer goods are pharmaceutical applications, wherein the decontamination agent is a decontamination agent steam or aerosol, and wherein the transport means (16) transports the decontaminated products towards the discharge opening (2).

10. The decontamination device according to claim 1, wherein the transport means (16) comprise an open topped product platform within the distributor chamber (11).

11. An isolator system, comprising an isolator and a decontamination device (1) according to claim 1 which is connected to said isolator in such a manner that decontaminated products or consumer goods, which are previously unpacked, are supplied to the isolator, in a sterile manner.

12. The isolator system according to claim 11, wherein the isolator system is for pharmaceutical applications, wherein the decontaminated products or consumer goods are previously unpacked in a product lock, and are supplied to a manipulator chamber of the isolator.

13. A method for operating a decontamination device (1) according to claim 1, wherein products to be decontaminated are introduced into the distributor chamber (11) through the supply opening, and wherein said products are then distributed to the different decontamination chambers (3, 4, 5, 6) in said distributor chamber by means of the distributor means (15) and are transported inside the discharge chamber (12), by means of the transport means (16) after a predefined decontamination period, the decontamination chambers (3, 4, 5, 6) being closed during said period, and wherein the decontamination agent concentration in the distributor chamber (11) and/or in the discharge chamber (12) is reduced.

14. The method according to claim 13, wherein the decontamination agent concentration in the decontamination chambers (3, 4, 5, 6) is also kept above a limit value, during loading and/or unloading of the decontamination chambers (3, 4, 5, 6) and/or wherein an active reduction of the decontamination agent concentration in the decontamination chambers (3, 4, 5, 6) before loading and/or unloading the decontamination chambers (3, 4, 5, 6) is omitted.

15. The method according to claim 13 wherein consumer goods are either unpacked from the decontaminated products in the discharge chamber (12) and are supplied to the isolator directly or indirectly via a product lock, or wherein the decontaminated products are transported from the discharge chamber (12) into a product lock (22) in which consumer goods are unpacked from the decontaminated products and then supplied to the isolator, or wherein the decontaminated products are supplied from the discharge chamber (12) to the isolator directly or indirectly via a product lock (22) and that said consumer goods are unpacked from the decontaminated products in the isolator.

16. The method according to claim 13, wherein products to be decontaminated are introduced into the distributor chamber one after the other, and wherein products are then distributed to the different decontamination chambers (**3, 4, 5, 6) and are transported inside the discharge chamber (12) towards the discharge opening (2).

17. The method according to claim 14, wherein the decontamination agent concentration is kept between 300 ppm and 1200 ppm.

* * * * *